(12) United States Patent
Hsieh

(10) Patent No.: US 7,020,243 B2
(45) Date of Patent: Mar. 28, 2006

(54) METHOD AND SYSTEM FOR TARGET ANGLE HEEL EFFECT COMPENSATION

(75) Inventor: Jiang Hsieh, Brookfield, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 204 days.

(21) Appl. No.: 10/728,611

(22) Filed: Dec. 5, 2003

(65) Prior Publication Data
US 2005/0123100 A1 Jun. 9, 2005

(51) Int. Cl.
G01N 23/083 (2006.01)

(52) U.S. Cl. .............................. 378/62; 378/4; 378/22; 378/98; 378/156

(58) Field of Classification Search .................... 378/4, 378/8, 15, 19, 21, 22, 62, 98, 98.2, 156
See application file for complete search history.

(56) References Cited

U.S. PATENT DOCUMENTS

| 4,130,759 | A | 12/1978 | Haimson |
|---|---|---|---|
| 4,706,026 | A | 11/1987 | Pelc et al. |
| 4,833,698 | A | 5/1989 | Flannery et al. |
| 4,891,829 | A | 1/1990 | Deckman et al. |
| 4,998,270 | A | 3/1991 | Scheid et al. |
| 5,021,327 | A | 6/1991 | Bunch et al. |
| 5,579,166 | A | 11/1996 | Beiting |
| 5,798,840 | A | 8/1998 | Beiting |
| 5,925,875 | A | 7/1999 | Frey |
| 5,987,347 | A | 11/1999 | Khoury et al. |
| 6,118,845 | A | 9/2000 | Simon et al. |
| 6,249,595 | B1 | 6/2001 | Foxall et al. |
| 6,320,931 | B1 | 11/2001 | Arnold |
| 6,359,958 | B1 | 3/2002 | Toth |
| 6,370,224 | B1 | 4/2002 | Simon et al. |
| 6,507,633 | B1 | 1/2003 | Elbakri et al. |
| 6,570,951 | B1 | 5/2003 | Hsieh |
| 6,662,038 | B1 | 12/2003 | Prince |
| 2005/0058254 | A1* | 3/2005 | Toth et al. .................. 378/156 |

* cited by examiner

*Primary Examiner*—David V Bruce
(74) *Attorney, Agent, or Firm*—Carl B. Horton, Esq.; Armstrong Teasdale LLP (57) ABSTRACT

A method of at least partially compensating for an x-ray tube target angle heel effect wherein the method includes providing an x-ray source, providing an x-ray detector having a plurality of detector rows positioned to receive x-rays from the source, and using a filter to increase uniformity of at least one of a projection noise and a spatial resolution, wherein the projection noise and the spatial resolution are non-uniform and are a function of a target angle along a z-axis.

20 Claims, 6 Drawing Sheets

METHOD AND SYSTEM FOR TARGET ANGLE HEEL EFFECT COMPENSATION

BACKGROUND OF THE INVENTION

This invention relates generally to Computed Tomography (CT) imaging systems, and more particularly, to target angle heel effect compensation.

In at least some known imaging systems, an x-ray tube source projects an x-ray beam which passes through an object being imaged, such as a patient, and impinges upon an array of x-ray detector rows. This technique is quite effective in medical CT scanners, but it has some drawbacks when the detector coverage becomes large, as in the case of multi-slice CT. With the advent of multi-slice CT imaging systems including a plurality of detector rows, at least two major drawbacks exist, a non-uniform x-ray flux and a non-uniform slice thickness. The non-uniform x-ray flux may result in a heel effect and a non-uniform slice thickness may result in variations in the spatial resolution.

The effects of the heel effect can produce image quality differences over the detector rows. For example, a 40 mm Volumetric Computed Tomography (VCT) detector with a nominal 7 degree target angle has an effective target angle of 5 degrees on the outer anode side row and 9 degrees on the outer cathode side row, resulting in an intensity variation of roughly 20% from one end of the detector to the other. This variance in radiation intensity due to the heel effect reduces image quality over the x-ray detector rows, and therefore reduces the image quality of the radiographs.

Non-uniform slice thickness results when a first projected focal spot height is significantly larger that a second projected focal spot height. Non-uniform slice thickness translates to a spatial resolution in the z-axis becoming a function of detector row.

In multi-slice CT, it is desirable to design a system such that both the x-ray flux and the spatial resolution do not change significantly from detector row to row.

BRIEF DESCRIPTION OF THE INVENTION

In one aspect, a method of at least partially compensating for an x-ray tube target angle heel effect is provided. The method includes providing an x-ray source, providing an x-ray detector having a plurality of detector rows positioned to receive x-rays from the source, and using a filter to increase uniformity of at least one of a projection noise and a spatial resolution, wherein the projection noise and the spatial resolution are non-uniform and are a function of a target angle along a z-axis.

In another aspect, an imaging system for scanning an object is provided. The imaging system includes an x-ray source, an x-ray detector having a plurality of detector rows positioned to receive x-rays from the source, a computer operationally coupled to the x-ray source and the x-ray detector, wherein the computer is configured to filter at least one of a projection noise and a spatial resolution to increase uniformity, and wherein the projection noise and the spatial resolution are non-uniform and are a function of target angle along a z-axis.

In yet another aspect, a computer readable medium encoded with a program executable by a system for at least partially compensating for an x-ray tube target angle heel effect is provided. The program is configured to instruct the computer to provide an x-ray source, provide an x-ray detector having a plurality of detector rows positioned to receive x-rays from the source, and use a filter to increase uniformity of at least one of a projection noise and a spatial resolution, wherein the projection noise and the spatial resolution are non-uniform and are a function of target angle along a z-axis.

DETAILED DESCRIPTION OF THE INVENTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index.

Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
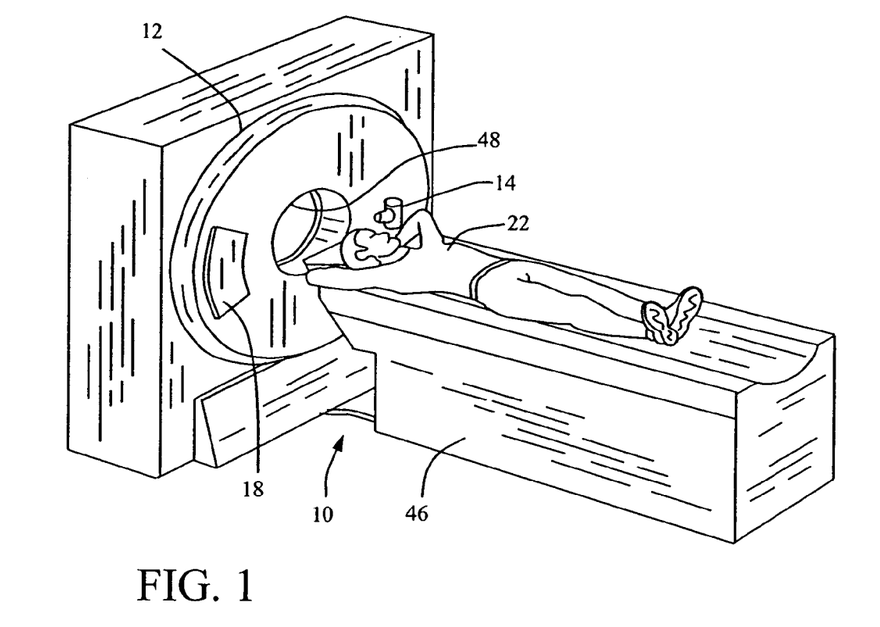
FIG. 1 is a pictorial view of a CT imaging system.
Figure 2:
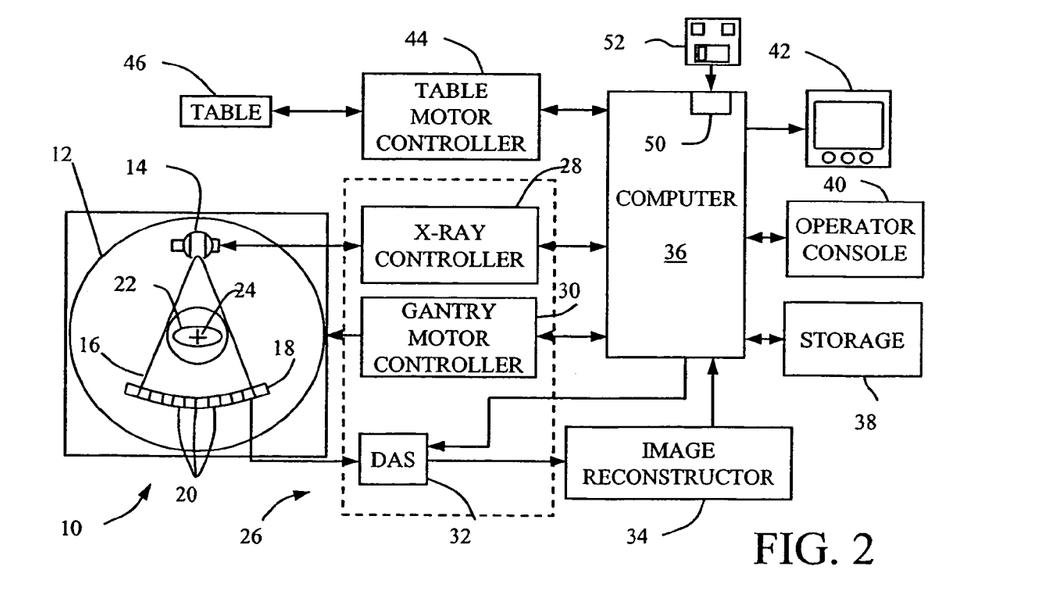
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown in FIGS. 1 and 2) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Herein described are methods and apparatus to at least partially compensate for the heel effect by increasing the uniformity of the standard deviation of the radiation measurements by the x-ray detector rows, in one embodiment, using a non-stationary filter.

Figure 3:
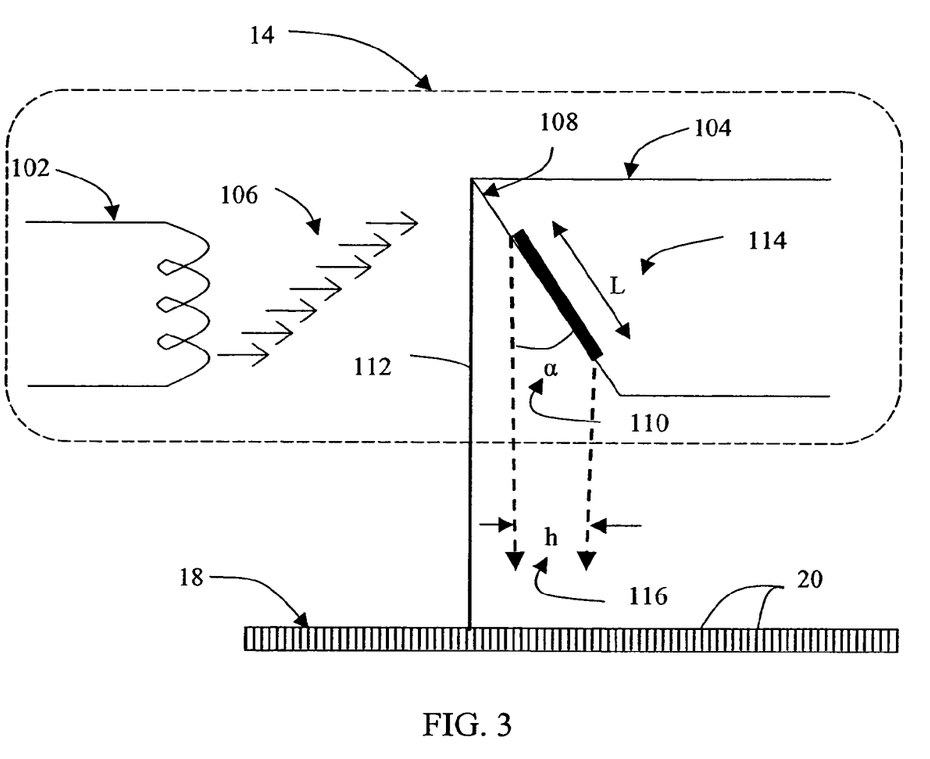
FIG. 3 illustrates an x-ray output.
Figure 4:
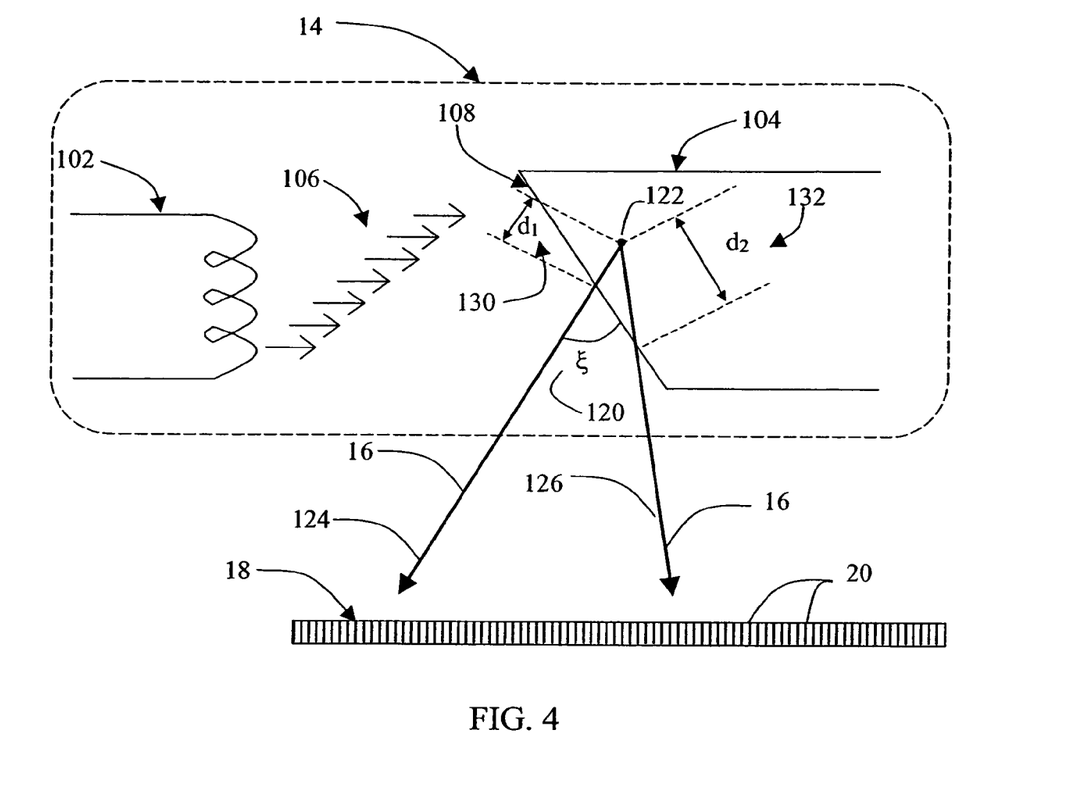
FIG. 4 illustrates the target angle heel effect.
Figure 5:
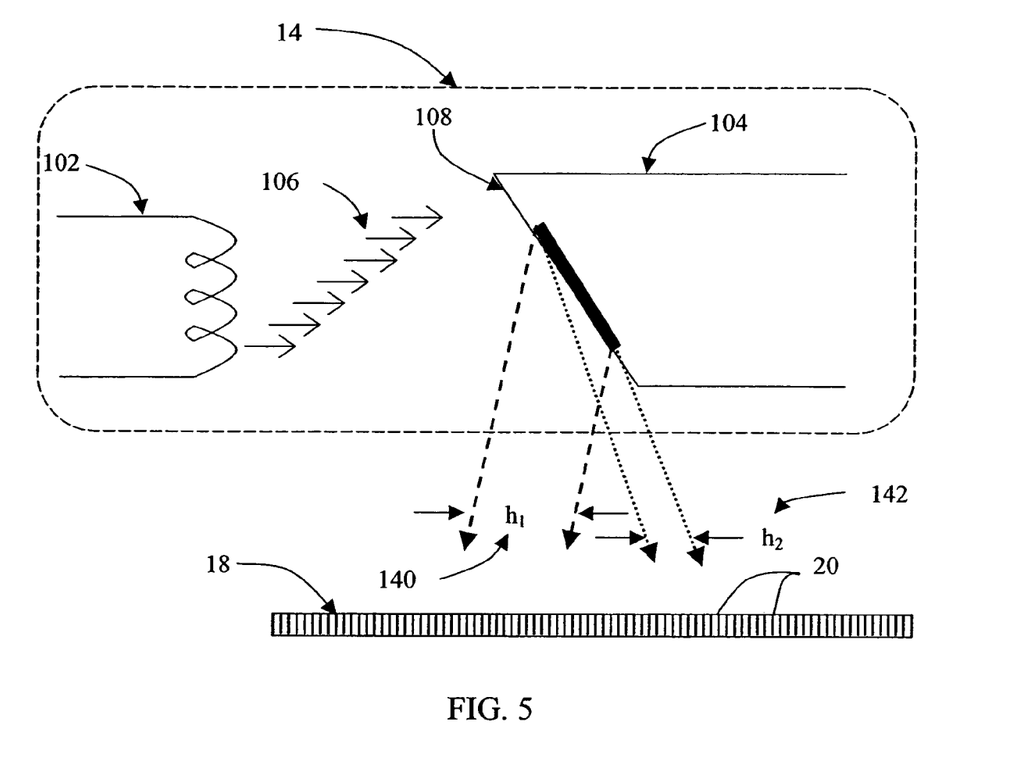
FIG. 5 illustrates the variation of the projected focal spot height along an z-axis.

Referring to FIGS. 3–5, x-ray tube 14 includes a cathode coil 102 and a target 104. In general, electrons 106 travel inside x-ray tube 14 from coil 102 to target 104. Electrons 106 make contact with target 104 at different locations, and cause the emission of x-rays 16 at different angles on leaving target 14 towards detector 18 and detector rows 20. Specifically in FIG. 3, electrons 106 contact a surface 108 of target 14 at a shallow angle α 110, with respect to a scan plan 112, along an actual focal spot length L 114. A projected height of the focal spot h 116 is equal to L 114 multiplied by $\sin(\alpha)$.

$$h = L \sin(\alpha) \quad (1)$$

The result is actual focal spot length L 114 is significantly larger than projected focal spot height h 116. There are two major impacts. One is a non-uniform x-ray flux across the slices in the z-axis (shown in FIG. 4) and the other is a non-uniform slice thickness (shown in FIG. 5).

FIG. 4 illustrates plurality of x-ray beams 16, a target angle ξ 120, and an average depth of interaction 122. Plurality of x-ray beams 16 include a first x-ray beam 124 and a second x-ray beam 126. X-ray 124 emitted from target 104 travels a first distance $d_1$ 130 within target 104 before exiting target 104. This is a shorter distance than a second distance $d_2$ 132 that an x-ray 126 travels within target 104 before exiting target 104. Since $d_2$ 132 is greater than $d_1$ 130, x-ray 126 leaves target 104 more attenuated than x-ray 124. This difference in attenuation is the heel effect. Consequently, the intensity of the x-ray flux changes as a function of target angle ξ 120 formed by x-ray 16 and target surface 108. Given the one-to-one relationship between target angle ξ 120 and detector row 20, the x-ray intensity changes monotonically with each detector row 20. In general, a smaller target angle ξ 120 corresponds to a reduced x-ray flux intensity.

FIG. 5 illustrates the non-uniformity of slice thickness. As discussed above, electrons 106 make contact with target 104 at different locations, and cause the emission of x-rays 16 at different angles on leaving target 14 towards detector 18 and detector rows 20. Non-uniformity of slice thickness is caused by the variation of the projected focal spot height h 116 (shown in FIG. 3). Specifically as shown in FIG. 5, a projected focal spot height $h_1$ 140, is significantly larger than projected focal spot height $h_2$ 142. This translates to a spatial resolution variation in the z-axis as function of detector row 20.

In multi-slice CT, it is desirable to design a system such that both the x-ray flux, which is linked closely to the projection noise, and the spatial resolution do not change significantly from detector row to row. To fully understand the impact of the heel effect, we use a simple model to estimate the spatial resolution of the system, although more complicated models may be used, the general conclusion will not change. In general, the system spatial resolution in z, s(z) is the convolution of the projected focal spot function, h(z), with the projected detector aperture function, d(z).

$$s(z)=h(z) \otimes d(z) \quad (2)$$

Projected focal spot function, h(z), is obtained assuming a point detector while a projected detector aperture is obtained assuming a point x-ray source. The system spatial resolution in z, s(z) is often called the slice-sensitivity-profile (SSP). If the focal point function and the detector aperture function are approximated by rectangular functions, then a full-width-half-maximum (FWHM) of the SSP equals to the larger FWHM of the two projected functions. Similarly, the full-width-at-zero-maximum (FWZM) is the sum of the widths of the two projected functions.

Figure 6:
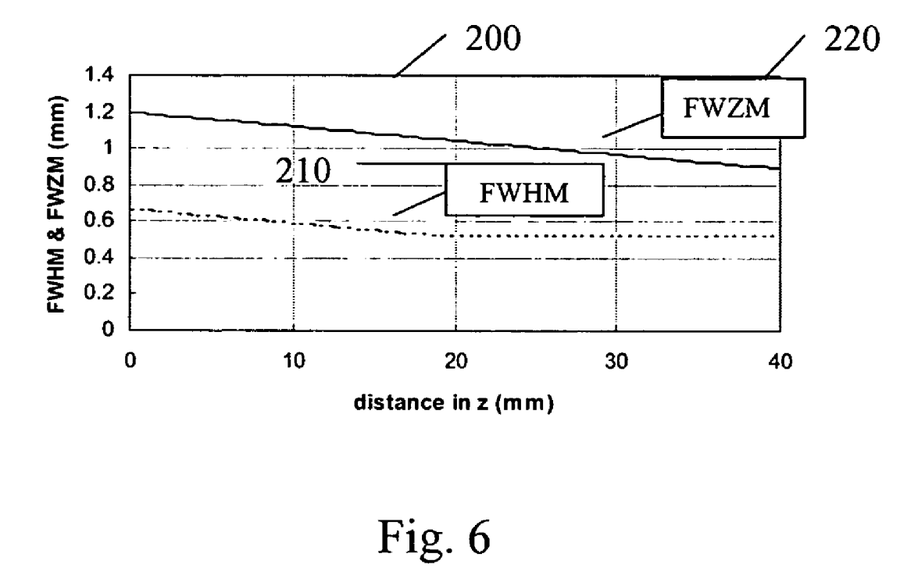
FIG. 6 is a chart illustrating the calculated FWHM and FWZM.

FIG. 6 is a chart 200 that illustrates the FWHM 210 of the SSP and the FWZM 220 of the two projected functions. Chart 20 clearly illustrates the significant non-uniformity of SSP. FWHM 210 and FWZM 220 are calculated for a detector aperture of 0.525 mm at an iso-center (0.625 mm detector pitch with 0.1 mm tungsten wire between detector rows), a nominal focal spot height of 1.2 mm measured at the center plane, a detector coverage of 40 mm at iso, and a 7° target angle.

The study of the non-uniformity of the x-ray flux is more complicated since it requires the estimation of the average depth of interaction, average x-ray photon energy, and the corresponding attenuation characteristics of the target. It has been determined that for a 7-degree target angle and 40 mm coverage at iso-center, the intensity variation is roughly 20% from one end of the detector to the other.

Our analysis indicates that SSP increases with target angle ξ 120 (shown in FIG. 4) while the projection noise reduces with target angle ξ 120. It is desirable to reduce both variations over detector rows 20. One approach to reduce the variation is the utilization of adaptive filtering. In general, the application of a low-pass filter reduces the spatial resolution and, at the same time, reduces the noise. We can design a non-stationary filter (along z) whose characteristics change as a function of detector row 20. That is, the amount of smoothing reduces as a function of target angle ξ 120. Since FWHM 220 and FWZM 230 do not change in the same fashion, the shape of a filter kernel also needs to change so that uniformity of both characteristics is met. The techniques to design such filters are well known, since both the original SSP, s(z), and the target SSP function, t(z), are known. For example, we can set the target response function as the original SSP function of the largest target angle ξ 120. The filtering function, $f(z)$, can then be derived with known signal processing techniques to satisfy the following relationship:

$$t(z)=s(z) \otimes f(z) \quad (3)$$

Figure 7:
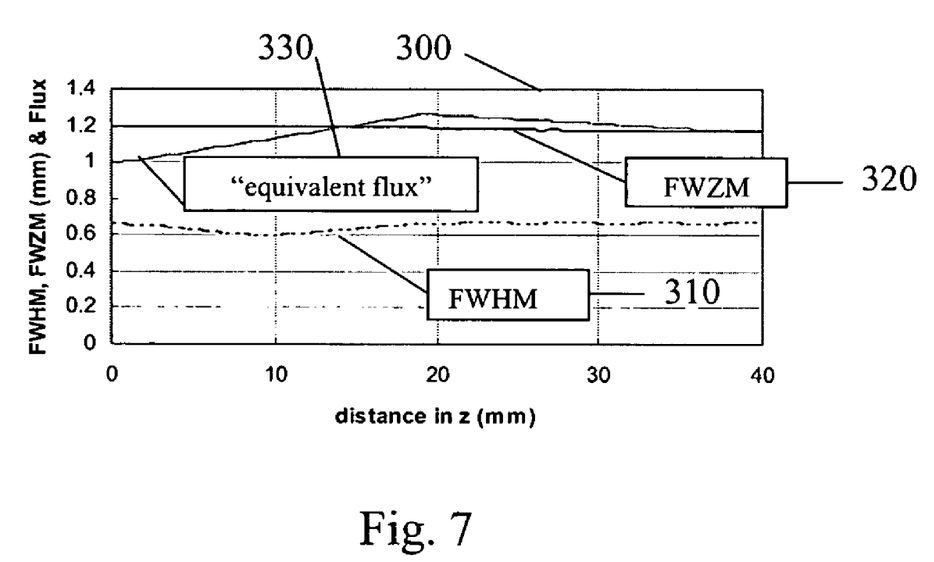
FIG. 7 is a chart illustrating the calculated FWHM, FWZM, and equivalent flux after adaptive filtering.

For example, one of the most well known techniques is the Weiner filter. The amount of smoothing increases with the reduction of target angle ξ 120 (shown in FIG. 4). Consequently, the amount of noise reduction also increases with the reduction of target angle ξ 120. This translates to a boost of equivalent photon flux. FIG. 7 is a chart 300 illustrating the resulting FWHM 310 and FWZM 320 after the filtering. Note that both parameters are much more uniform over z. At the same time, equivalent photon flux boost 330 from one end of detector 20 (shown in FIG. 4) to the other is roughly 20%. Given the previous study that the flux drop is roughly 20%, the resulting noise in the projection becomes more uniform with the filtering.

Target function, t(z), can be chosen to be different from the SSP of the largest target angle ξ 120. For example, the target function can be selected as the SSP of the center row. In this case, the filter functions for target angle ξ 120 larger than the center row will be high-pass filters. The filter functions for target angle ξ 120 smaller than the center row will be low-pass filter. Consequently, the noise level is increased for projections collected with rows of larger target angle ξ 120, and the noise level is reduced for projections collected with rows of smaller target angle ξ 120.

Alternatively, the filtering function can be determined based on the x-ray flux instead of the SSP. Based on previous analysis, we know that the x-ray flux decreases with the decrease in target angle ξ 120. Therefore, a set of filter functions is derived such that they equalize the projection noise across all detector rows. For example, a 3-point filter may be used to produce the final projection based on the projections of the neighboring three detector rows. Filter coefficients for detector rows k−1, k, and k+1, are denoted by $W_{k-}$, $W_k$, $W_{k+}$, and $\eta_k$ the normalized x-ray flux level for detector row k (the reference row has a normalized flux level of unity), the filter needs to satisfy the following relationship:

$$w^2_{k-}+w^2_k+w^2_{k+}=\eta_k \quad (4)$$

Alternatively, the filter design can be dependent on the combined x-ray flux and SSP. For example, the filter is determined based on the x-ray flux for target angle ξ 120 larger than the center row and the filter is determined based on the SSP function for target angle ξ 120 smaller than the center row.

The application of the non-stationary filter can be combined with the non-uniform detector size. That is, the multi-slice detector can be designed such that the detector aperture changes from row to row. In this combination, the uniformity of the x-ray flux and system response are achieved with both techniques. Thus allowing for a more relaxed filter design.

Figure 8:
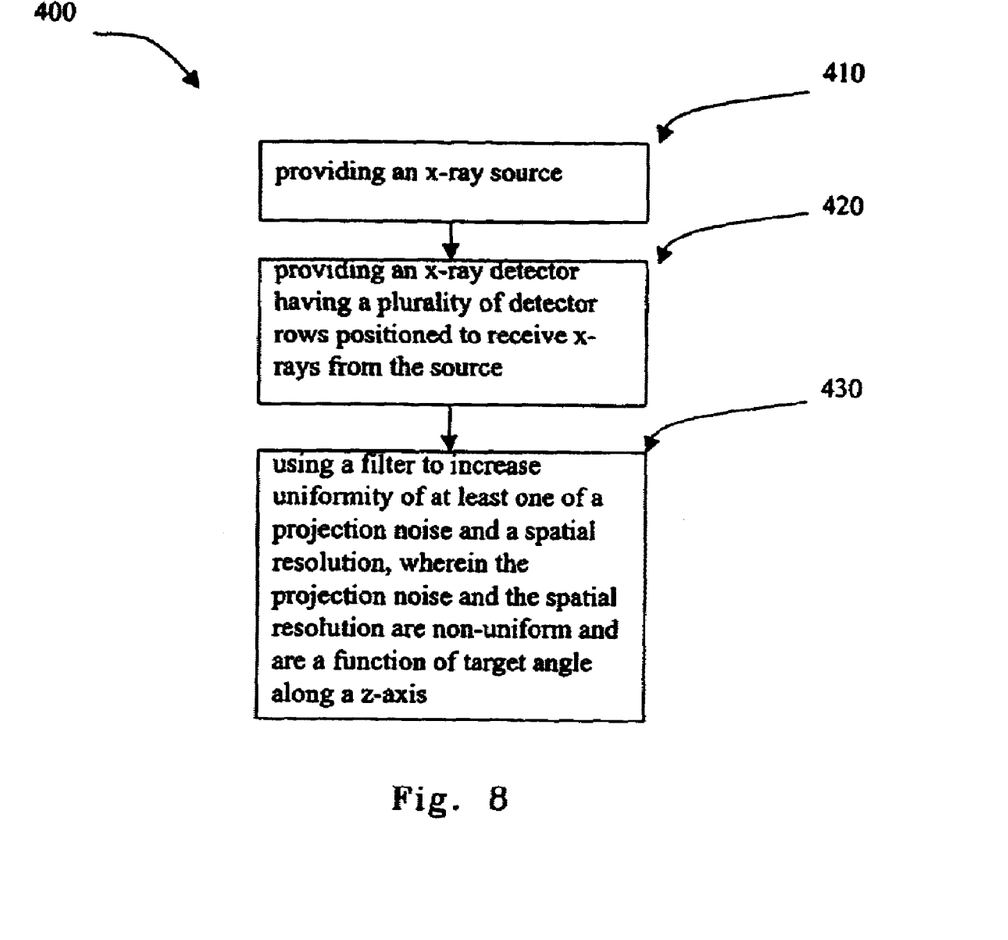
FIG. 8 is a block schematic diagram of a method of reducing heel effect compensation.

FIG. 8 is a method 400 for facilitating a reduction in artifacts using imaging system 10. Method 400 includes providing 410 an x-ray source, providing 420 an x-ray detector having a plurality of detector rows positioned to receive x-rays from the source, and using 430 a filter to increase uniformity of at least one of projection noise and a spatial resolution, wherein the x-ray flux and the spatial resolution are non-uniform and are a function of target angle along a z-axis.

Previous attempts to reduce the x-ray tube heel effects have been focused on the modification of the x-ray tube target angle. This approach trades uniformity of the x-ray flux and system response with the x-ray tube efficiency. The proposed approach eliminates such tradeoff. In addition, redesign of the x-ray tube is eliminated.

Exemplary embodiments of a heel effect compensation filter are described above in detail. The assemblies are not limited to the specific embodiments described herein, but rather, components of each assembly may be utilized independently and separately from other components described herein.

While the invention has been described in terms of various specific embodiments, those skilled in the art will recognize that the invention can be practiced with modification within the spirit and scope of the claims.

What is claimed is:

1. A method of at least partially compensating for an x-ray tube target angle heel effect, said method comprising:
   providing an x-ray source;
   providing an x-ray detector having a plurality of detector rows positioned to receive x-rays from the source; and
   using a filter to increase uniformity of at least one of a projection noise and a spatial resolution, wherein the projection noise and the spatial resolution are non-uniform and are a function of a target angle along a z-axis.

2. A method in accordance with claim 1, wherein said using a filter comprises filtering different detector rows differently based on detector row number.

3. A method in accordance with claim 1, wherein said using a filter comprises using a filter to increase uniformity of the spatial resolution where the filter $f(z)$ is determined according to $t(z)=s(z)\otimes f(z)$, wherein $t(z)$ is a target spatial resolution function, and $s(z)=h(z)\otimes d(z)$, wherein $h(z)$ is a projected focal spot function and $d(z)$ is a projected detector aperture function.

4. A method in accordance with claim 1, wherein said using a filter comprises using a filter to increase uniformity of the projection noise such that $$w^2_{k-}+w^2_k+w^2_{k+}=\eta_k$$

wherein $w_{k-}$, $w_k$, $w_{k+}$ denote a filter coefficients for detector rows k−1, k, and k+1; and
wherein $\eta_k$ is a normalized projection noise level for detector row k.

5. A method in accordance with claim 1 wherein said using a filter further comprises using a filter configured to increase uniformity of the spatial resolution when the target angle is smaller than the center detector row and increase uniformity of the projection noise when the target angle is larger than a center detector row.

6. A method in accordance with claim 5 wherein said using a filter further comprises using a filter configured to increase uniformity of the spatial resolution when a target angle is smaller than the center detector row, wherein the filter $f(z)$ is determined according to $t(z)=s(z)\otimes f(z)$, wherein $t(z)$ is a target spatial resolution function, and $s(z)=h(z)\otimes d(z)$, wherein $h(z)$ is a projected focal spot function and $d(z)$ is a projected detector aperture function.

7. A method in accordance with claim 6 wherein said using a filter further comprises using a filter configured to increase uniformity of the projection noise when a target angle is larger than a center detector row such that $$w^2_{k-}+w^2_k+w^2_{k+}=\eta_k$$

wherein $w_{k-}$, $w_k$, $w_k$ denote a filter coefficients for detector rows k−1, k, and k+1; and
wherein $\eta_k$ is a normalized projection noise level for detector row k.

8. An imaging system for scanning an object comprising:
   an x-ray source;
   an x-ray detector having a plurality of detector rows positioned to receive x-rays from said source;
   a computer operationally coupled to said x-ray source and said x-ray detector; and
   a filter positioned between said x-ray source and said x-ray detector, said filter comprising a non-stationary filter, wherein said non-stationary filter is configured to filter different detector rows differently based on detector row number.

9. An imaging system for scanning an object comprising:
   an x-ray source;
   an x-ray detector having a plurality of detector rows positioned to receive x-rays from said source;
   a computer operationally coupled to said x-ray source and said x-ray detector, wherein said computer is configured to filter at least one of a projection noise and a spatial resolution to increase uniformity, wherein said projection noise and said spatial resolution are non-uniform and are a function of target angle along a z-axis.

10. A system in accordance with claim 9, wherein said filter is configured to increase uniformity of said spatial resolution where the filter $f(z)$ is determined according to $t(z)=s(z)\otimes f(z)$, wherein $t(z)$ is a target spatial resolution function, and $s(z)=h(z)\otimes d(z)$, wherein $h(z)$ is a projected focal spot function and $d(z)$ is a projected detector aperture function.

11. A system in accordance with claim 9, wherein said filter is configured to increase uniformity of said projection noise such that $$w^2_{k-}+w^2_k+w^2_{k+}=\eta_k$$

wherein $w_{k-}$, $w_k$, $w_k$ denote a filter coefficients for detector rows k−1, k, and k+1; and
wherein $\eta_k$ is a normalized projection noise level for detector row k.

12. A system in accordance with claim 9 wherein said filter is further configured to increase uniformity of said spatial resolution when a target angle is smaller than a center detector row and increase uniformity of said projection noise when the target angle is larger than the center detector row.

13. A system in accordance with claim 12 wherein said filter is further configured to increase uniformity of said spatial resolution when the target angle is smaller than the center detector row, wherein the filter $f(z)$ is determined according to $t(z)=s(z) \otimes f(z)$, wherein $t(z)$ is a target spatial resolution function, and $s(z)=h(z) \otimes d(z)$, wherein $h(z)$ is a projected focal spot function and $d(z)$ is a projected detector aperture function.

14. A system in accordance with claim 12 wherein said filter is further configured to increase uniformity of said projection noise when the target angle is larger than the center detector row according to $$w^2_{k-}+w^2_k+w^2_{k+}=\eta_k$$

wherein $w_{k-}$, $w_k$, $w_k$ denote a filter coefficients for detector rows k−1, k, and k+1; and wherein $\eta_k$ is a normalized projection noise level for detector row k.

15. A computer readable medium encoded with a program executable by a system for at least partially compensating for an x-ray tube target angle heel effect, said program configured to instruct the computer to:

provide an x-ray source;

provide an x-ray detector having a plurality of detector rows positioned to receive x-rays from the source; and use a filter to increase uniformity of at least one of a projection noise and a spatial resolution, wherein the projection noise and the spatial resolution are non-uniform and are a function of target angle along a z-axis.

16. A computer readable medium in accordance with claim 15, wherein to use a filter comprises using said filter to increase uniformity of the spatial resolution where the filter $f(z)$ is determined according to $t(z)=s(z) \otimes f(z)$, wherein $t(z)$ is a target spatial resolution function, and $s(z)=h(z) \otimes d(z)$, wherein $h(z)$ is a projected focal spot function and $d(z)$ is a projected detector aperture function.

17. A computer readable medium in accordance with claim 15, wherein to use a filter comprises using said filter to increase uniformity of the projection noise according to $$w^2_{k-}+w^2_k+w^2_{k+}=\eta_k$$

wherein $w_{k-}$, $w_k$, $w_k$ denote a filter coefficients for detector rows k−1, k, and k+1; and wherein $\eta_k$ is a normalized projection noise level for detector row k.

18. A computer readable medium in accordance with claim 15 wherein said to use a filter further comprises using said filter configured to increase uniformity of the spatial resolution when the target angle is smaller than the center detector row and increase uniformity of the projection noise when the target angle is larger than a center detector row.

19. A computer readable medium in accordance with claim 18 wherein said to use a filter further comprises using said filter configured to increase uniformity of the spatial resolution when a target angle is smaller than the center detector row, wherein the filter $f(z)$ is determined according to $t(z)=s(z) \otimes f(z)$, wherein $t(z)$ is a target spatial resolution function, and $s(z)=h(z) \otimes d(z)$, wherein $h(z)$ is a projected focal spot function and $d(z)$ is a projected detector aperture function.

20. A computer readable medium in accordance with claim 19 wherein said to use a filter further comprises using said filter configured to increase uniformity of the projection noise when a target angle is larger than a center detector row such that $$w^2_{k-}+w^2_k+w^2_{k+}=\eta_k$$

wherein $w_{k-}$, $w_k$, $w_k$ denote a filter coefficients for detector rows k−1, k, and k+1; and wherein $\eta_k$ is a normalized projection noise level for detector row k.

* * * * *